United States Patent [19]

Régnier et al.

[11] Patent Number: 4,593,026
[45] Date of Patent: Jun. 3, 1986

[54] ANTI-HYPOXIC DISUBSTITUTED POLYMETHYLENE IMINE DERIVATIVES, COMPOSITIONS, AND METHOD OF USE THEREFOR

[75] Inventors: Gilbert Régnier, Malabry; Alain Dhainaut, Chatou; Michel Laubie, Vaucresson; Jacques Duhault, Croissy sur Seine; Francois Roman, Courbevoie, all of France

[73] Assignee: Adir, S.A.R.L., Neuilly-sur-Seine, France

[21] Appl. No.: 597,273

[22] Filed: Apr. 6, 1984

Related U.S. Application Data

[63] Continuation-in-part of Ser. No. 478,715, Mar. 25, 1983, Pat. No. 4,514,398.

[30] Foreign Application Priority Data

Apr. 12, 1983 [FR] France .................. 83 05904

[51] Int. Cl.$^4$ .................. C07D 401/04; C07D 403/04; A61K 31/53
[52] U.S. Cl. .................. 514/245; 260/239 B; 514/212; 514/227; 544/113; 544/198
[58] Field of Search .................. 544/113, 198; 260/239 B; 424/244, 249, 248.4; 514/212, 227, 245

[56] References Cited

FOREIGN PATENT DOCUMENTS 0090733 10/1983 European Pat. Off. .......... 544/198

*Primary Examiner*—Henry R. Jiles
*Assistant Examiner*—J. G. Mullins
*Attorney, Agent, or Firm*—Gordon W. Hueschen

[57] ABSTRACT

Disubstituted polymethylene imines of the formula:

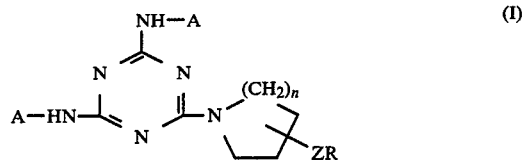

in which:
A is a straight or branched chain ($C_3$–$C_5$) hydrocarbon containing radical optionally containing one or two double bond and optionally substituted by one or more hydroxy;
n is zero, one or two;
Z is oxygen or NH; and
R is:
either COR', in which R' is:
(a) a straight or branched chain ($C_1$–$C_6$), hydrocarbon containing radical, optionally containing one oxygen or sulfen or a double bond and optionally substituted by phenyl or substituted phenyl; or
(b) phenyl, halophenyl, lower alkoxyphenyl, (di-or-tri-methylene) dioxyphenyl or;
(c) furyl, thienyl, benzofuryl, benzothienyl or benzodioxannyl; or
(d)

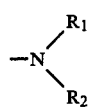

in which $R_1$ and $R_2$ are hydrogen or lower alkyl or

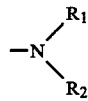

is a five or six membered heterocyclic radical which may contain an oxygen;
or
—$SO_2R''$ in which R'' is ($C_1$–$C_3$) alkyl or phenyl.

These compounds and physiologically tolerable salts thereof may be used as medicines especially in the treatment of all kinds tissular hypoxy.

5 Claims, No Drawings

ANTI-HYPOXIC DISUBSTITUTED POLYMETHYLENE IMINE DERIVATIVES, COMPOSITIONS, AND METHOD OF USE THEREFOR

The present application is a continuation-in-part of out prior-filed United States patent application Ser. No. 478,715, filed Mar. 25, 1983, now U.S. Pat. No. 4,514,398, issued Apr. 30, 1985.

The present invention provides disubstituted polymethylene imines of the formula I:

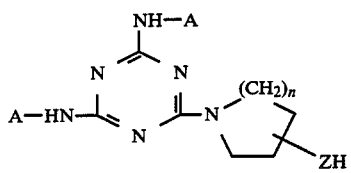 (I)

in which
A is selected from the group consisting of straight and branched hydrocarbon containing radicals having from 3 to 5 carbon atoms inclusive, these radicals containing one and two double bonds, and these radicals mono and poly substituted by hydroxy;

n is selected form the group consisting of zero and the integers one and two;

Z is selected from the group consisting of oxygen and NH; and

R is selected from the group consisting of:
(a) —CO R′ in which R′ is selected from the group consisting of:
straight and branched hydrocarbon containing radicals having from 1 to 6 carbon atoms inclusive, optionally containing an oxygen atom, a sulfur atom or a double bond and optionally substituted by phenyl, halophenyl, ($C_1$–$C_5$ alkoxy)-phenyl [—O—($CH_2$)—O—]-phenyl, or [—O—($CH_2$)$_3$—O—]-phenyl radicals;
phenyl, halophenyl, ($C_1$–$C_5$-alkoxy)-phenyl, [—O—($CH_2$)$_2$—O—]-phenyl and [—O—($CH_2$)$_3$—O—]phenyl radicals;
furyl, thienyl, benzofuryl, benzothienyl and benzodioxannyl radicals; and

in which $R_1$ and $R_2$,
which are the same or different, are each selected from the group consisting of: a hydrogen atom, and ($C_1$–$C_6$)-alkyl radicals and

may also represent five and six-membered heterocyclic radicals optionally containing an oxygen atom, such, for example, as: pyrrolidinyl, piperidino and morpholino radicals; or
(b) $SO_2R''$ in which R″ is selected from the group consisting of alkyl radicals having from 1 to 3 carbon atoms inclusive, in straight and branched chains, and a phenyl radical.

The present invention relates also to a process for the preparation of derivatives of the general formula I characterised in that:
a polymethylene imine of the general formula II:

 (II)

in which n, Z and R have the meanings given hereinbefore, is condensed with a halogenated derivative of the general formula III:

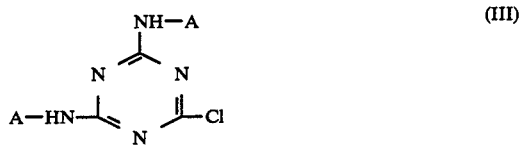 (III)

in which A has the meaning given hereinbefore.

The condensation is preferably carried out in an alcohol such as butanol or an aliphatic amide such as dimethylformamide. Advantageously, the operation is carried out at a temperature between 120° and 140° C. in the presence of an acceptor for the hydracid formed in the course of the reaction. This acceptor may be, for example, triethylamine or an excess of the polymethylene imine of the formula II used for the condensation.

The present invention relates also to a process for the preparation of derivatives of the general formula I characterised in that:
a polymethylene imine of the general formula IV:

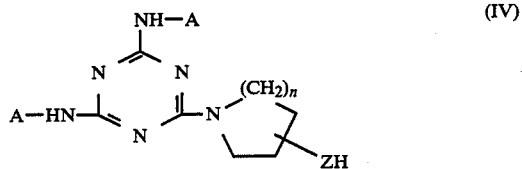 (IV)

in which A, n and Z have the meanings given hereinbefore, is condensed with a halogenated derivative of the general formula V:

Cl—R (V)

in which R has the meaning given hereinbefore.

It is particularly advantageous to carry out the condensation in an appropriate solvent such as, for example, pyridine, tetrahydrofuran or dimethylformamide at a temperature between 20° and 50° C., in the presence of an acceptor for the hydracid formed in the course of the reaction. There may be mentioned as acceptor, for example, triethylamine or pyridine.

These novel derivatives obtained in this manner may be converted into acid addition salts; these salts therefore form part of the invention. There may be mentioned as acids that can be used for the formation of these salts, for example, in the mineral series hydrochloric, hydrobromic, sulphuric and phosphoric acid and, in the organic series, acetic, propionic, maleic, fumaric, tartaric, nitric, oxalic, benzoic, methanesulphonic and isethionic acid.

These novel derivatives can be purified by physical methods such as crystallisation and chromatography, or by chemical methods such as the formation of addition salts with acids and decomposition of these salts by alkaline agents.

Starting mterials used in the processes described above are either known products or products prepared from known substances according to processes described for the preparation of analogous products as indicated in the following Examples.

The derivatives of the general formula I and the physiologically tolerable addition salts thereof have valuable pharmacological and therapeutic properties. In particular they promote the uptake of oxygen and can thus be used as medicaments, especially in the treatment of any type of tissue hypoxia.

These derivatives and their physiologically tolerable salts have, moreover, a very low toxicity.

The effect of the derivatives of the invention on oxygen pressure ($PO_2$) was studied in dogs anesthetized with Nembutal. Specimens of blood are taken periodically 2, 5, 15, 45 and 75 minutes after administration of the compounds being tested; they are used to determine the pH, the $PO_2$ and the $PCO_2$.

The $PO_2$ is measured in a $BMS_3$ radiometer apparatus. The reading of $PO_2$ is made on this apparatus, which has previously been calibrated with known values, by means of a platinum electrode or a Clark electrode.

The products of the present invention are found to be equally effective in the treatment of anaemic hypoxia, induced by chemical means by the subcutaneous injection of $NaNO_2$ according to the method described by Gibson G. E. Neurobiol Aging 2, 165, (1981) and Biochem. Pharmacol, 28, 747, (1979), and of hypobar hypoxia in accordance with the technique described by Legeai J. M. et. al., Experientia, 37, 292 (1981).

The invention relates also to pharmaceutical compositions containing as active ingredient a derivative of the general formula I or one of the physiologically tolerable salts thereof, mixed or associated with an appropriate pharmaceutical excipient.

It relates in particular to dosage forms.

The pharmaceutical compositions thus obtained are advantageously provided in various dosage forms such as, for example, tablets, dragées, gelatin-coated pills, suppositories, and injectable or drinkable solutions.

The following Examples illustrate the invention without giving any limitation.

EXAMPLE 1

1-(4,6-bis-allylamino-2-s.triazinyl)-4-acetoxy-piperidine

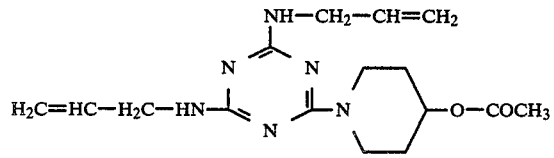

First method

A solution of 10 g of 4,6-bis-allylamino-2-chlorotriazine and 8 g of the hydrochloride of 4-acetoxy-piperidine, which melts (Kofler) at 160° C., in 150 ml of n-butanol is heated for 5 hours at 110° C. in the presence of 9 g of triethylamine. The solvent is then evaporated under reduced pressure and the residue is taken up in water. The insoluble portion is extracted with $CHCl_3$. After evaporation of the chloroformic solution, the residue is dissolved in a mixture of dichloromethane/ethyl acetate (7/3), then chromatographed on silica under a pressure of 101.000 Pa. 9 g of pure resinous base are obtained, which is converted into the fumarate in ethanol. Finally, there are isolated 10 g of the fumarate of 1-(4,6-bis-allylamino-2-s.triazinyl)-4-acetoxy-piperidine in the form of white crystals which melt (Kofler) at 163° C. The hydrochloride of 4-acetoxy-piperidine was prepared by the hydrogenolysis of 4-acetoxy-1-benzyl-piperidine B.p. 0.15 mmHg 125°–130° C., itself prepared by the pyridinated acetylation of 1-benzyl-4-piperidinol.

Second method

A solution of 8.7 g of 1-(4,6-bis-allylamino-2-s.triazinyl)-4-piperidinol, melting (Kofler) at 130° C., in 90 ml of pyridine is stirred at room temperature for 17 hours in the presence of 5 g of acetyl chloride. Subsequently the pyridine is removed under reduced pressure, the residue is taken up in water and chloroform, and the chloroform phase is washed copiously with water and evaporated under reduced pressure. The brown oil thus obtained (9.7 g) is dissolved in 100 ml of ethanol under reflux and the fumarate is formed by the addition of 7 g of fumaric acid. After crystalisation, 7.6 g of the fumarate of 1-(4,6-bis-allylamino-2-s.triazinyl)-4-acetoxy-piperidine are obtained in the form of white crystals which melt (Kofler) at 163° C.

The 1-(4,6-bis-allylamino-2-s.triazinyl)-4-piperidinol used as starting material was prepared by condensing 4,6-bis-allylamino-2-chlorotriazine with 4-hydroxy-piperidine in butanol at 116° C. in the presence of potassium carbonate.

EXAMPLES 2 TO 16

The following derivatives were prepared in accordance with the methods described in Example 1:

(2) 1-(4,6-bis-allylamino-2-s.triazinyl)-4-propionyloxy-piperidine, the fumarate of which melts (capillary) at 165°–167° C. (anhydrous ethanol).

(3) 1-(4,6-bis-allylamino-2-s.triazinyl)-4-benzoyloxy-piperidine, the fumarate of which melts (capillary) at 135°–138° C. (anhydrous ethanol).

(4) 1-(4,6-bis-allylamino-2-s.triazinyl)-4-(3,4-methylenedioxy-benzoyloxy)-piperidine, the fumarate of which melts (capillary) at 134°–137° C. (anhydrous ethanol).

(5) 1-(4,6-bis-allylamino-2-s.triazinyl)-4-cinnamoyloxy-piperidine, the fumarate of which melts (capillary) at 149°–153° C. (anhydrous ethanol).

(6) 1-(4,6-bis-allylamino-2-s.triazinyl)-4-(3-methoxypropionyloxy)-piperidine, the fumarate of which melts (capillary) at 152°–153° C. (anhydrous ethanol).

(7) 1-(4,6-bis-allylamino-2-s.triazinyl)-4-acetamido-piperidine, m.p. (capillary) 181°–183° C. (butanol).

(8) 1-(4,6-bis-allylamino-2-s.triazinyl)-3-methylsulphonyloxy-azetidine, m.p. (Kofler): 150° C.

(9) 1-(4,6-bis-allylamino-2-s.triazinyl)-4-methylsulphonyloxy-piperidine, m.p. (Kofler) of the corresponding chlorohydrate: 172° C.

(10) 1-(4,6-bis-allylamino-2-s.triazinyl)-4-trimethylacetoxy-piperidine, m.p. (capillary) of the corresponding fumarate: 117°–180° C. (anhydrous ethanol).

(11) 1-(4,6-bis-allylamino-2-s.triazinyl)-4-(p-chlorophenoxyacetoxy)-piperidine, m.p. (capillary) of the corresponding fumarate: 153°-155° C. (anhydrous ethanol).

(12) 1-(4,6-bis-allylamino-2-s.triazinyl)-4-(2-furoyl oxy)-piperidine, m.p. (capillary) of the corresponding fumarate: 127°-129° C. (anhydrous ethanol).

(13) 1-(4,6-bis-allylamino-2-s.triazinyl)-4-(2-benzothienyl-carbonyloxy)-piperidine, m.p. (capillary) of the corresponding fumarate: 172°-175° C. (anhydrous ethanol).

(14) 1-(4,6-bis-allylamino-2-s.triazinyl)-4-(2-benzodioxanyl-carbonyloxy)-piperidine, m.p. (capillary) of the corresponding fumarate: 168°-171° C. (anhydrous ethanol).

(15) 1-(4,6-bis-allylamino-2-s.triazinyl)-4-methoxyacetoxy-piperidine, m.p. (capillary) of the corresponding fumarate: 160°-162° C. (anhydrous ethanol).

(16) 1-(4,6-bis-allylamino-2-s.triazinyl)-4-(6-benzodioxinyl-carbonyloxy)-piperidine, m.p. (capillary) of the corresponding fumarate: 167°-170° C. (anhydrous ethanol).

We claim:

1. A compound selected from the group consisting of a disubstituted polymethylene imine of the formula I:

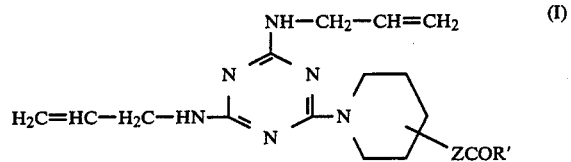

in which:
Z is oxygen and simultaneously
R' is selected from the group consisting of: straight and branched hydrocarbon radicals having
1 to 6 carbon atoms inclusive, optionally containing an oxygen atom, optionally substituted by halophenyl; and
phenyl and methylenedioxyphenyl radicals; and
furyl, benzodioxanyl, and benzodioxinyl radicals; or
Z is NH and simultaneously
R' is lower-alkyl having 1 to 6 carbon atoms inclusive; and a physiologically tolerable acid addition salt thereof.

2. A compound of claim 1 which is 1-(4,6-bis allylamino-2-s.triazinyl)-4-acetoxy piperidine, or its fumarate.

3. A compound of claim 1 which is 1-(4,6-bis allylamino-2-s.triazinyl)-4-acetamideo piperidine.

4. Anti-hypoxic pharmaceutical compositions containing as active ingredient an effective anti-hypoxic amount of a compound of claim 1 together with a suitable pharmaceutical carrier.

5. A method for treating a living animal body afflicted with a tissular hypoxy, comprising the steps of administering to the said living animal an amount of a compound of claim 1 which is effective for the alleviation of the said condition.

* * * * *